United States Patent [19]

Maule

[11] Patent Number: 5,374,563
[45] Date of Patent: Dec. 20, 1994

[54] SURFACE PLASMON RESONANCE DEVICE AND METHOD OF DETERMINING BIOLOGICAL, BIOCHEMICAL, OR CHEMICAL ANALYTE

[75] Inventor: Coin H. Maule, Cambridge, Great Britain

[73] Assignee: Fisons plc, Ipswich, United Kingdom

[21] Appl. No.: 984,430

[22] PCT Filed: Aug. 30, 1991

[86] PCT No.: PCT/GP91/01466

§ 371 Date: Apr. 9, 1993

§ 102(e) Date: Apr. 9, 1993

[87] PCT Pub. No.: WO92/04617

PCT Pub. Date: Mar. 19, 1992

[30] Foreign Application Priority Data

Sep. 1, 1990 [GB] United Kingdom ............... 9019123

[51] Int. Cl.$^5$ .......................................... C01N 21/55
[52] U.S. Cl. .................................... 436/165; 436/805; 436/807; 435/4; 435/7.1; 435/808; 422/82.05; 356/318; 356/445
[58] Field of Search ............... 356/128, 317, 318, 369, 356/435, 68.1; 422/82.05, 88, 164; 436/165, 169, 170, 805, 807; 435/4, 7.8, 7.1, 808

[56] References Cited

U.S. PATENT DOCUMENTS 4,889,427 12/1989 Van Veen et al. ................. 356/445

FOREIGN PATENT DOCUMENTS 0305109 3/1989 European Pat. Off. .
2156970 10/1985 United Kingdom .
EP88/00108 8/1989 WIPO .

OTHER PUBLICATIONS

*Sensors and Actuators*, vol. 4, 1983, Lidberg et al., "Surface Plasmon Resonance for Gas Detection and Biosensing," pp. 299–304.

Primary Examiner—David A. Redding
Attorney, Agent, or Firm—Marshall, O'Toole, Gerstein, Murray & Borun

[57] ABSTRACT

A sensor based on the technique of surface plasmon resonance (SPR) comprises an SPR device, a source of electromagnetic radiation from which radiation can be directed onto the device, and a detector to measure the intensity of radiation reflected from the SPR device. The electromagnetic radiation directed onto the SPR device contains both Transverse Electric-polarized and Transverse Electric-polarized components. A polarization analyzer is interposed between the device and the detector such that, at angles away from resonance, little or no light reaches the detector. The sensor is particularly useful in the qualitative and/or quantitative determination of biological, biochemical or chemical analytes.

11 Claims, 3 Drawing Sheets

SURFACE PLASMON RESONANCE DEVICE AND METHOD OF DETERMINING BIOLOGICAL, BIOCHEMICAL, OR CHEMICAL ANALYTE

This invention relates to sensors for the detection of chemical species, in particular to sensors for the detection of analytes in solution by the technique of surface plasmon resonance (SPR).

BACKGROUND OF THE INVENTION

SPR is well-known for the detection of chemical species. SPR may be achieved by using the evanescent wave which is generated when a TM-polarised (or p-polarised) light beam is totally internally reflected at the interface between a dielectric medium, e.g. glass, and a thin layer of metal. Any TE-polarised (or s-polarised) component of the radiation cannot excite SPR by the process of total internal reflection and in conventional SPR such components are not employed. The technique is described by Lieberg et al in Sensors and Actuators, 4, 299.

The basis for the application of SPR to sensing is the fact that the oscillation of the surface-plasma of free electrons which exists at a metal-dielectric boundary is affected by the refractive index of the material adjacent to the metal surface. Resonance occurs when the angle of incidence of the radiation has a particular value, and this value is dependent on the refractive index of the material adjacent to the metal. Thus, changes in this refractive index give rise to changes in the angle at which resonance occurs.

A problem which occurs with known SPR devices is that resonance is detected as a reduction in the intensity of the reflected light. This means that the electronic gain of the detector, or the light level from the source, can only be set with respect to the bright background to prevent electronic saturation away from resonance. Small changes in intensity at resonance are difficult to amplify independently for measurement.

We have now devised an SPR device in which resonance is detected as an increase in light intensity. This enables the electronic gain of the detector to be set to suit the strength of the resonance, with associated improvements in sensitivity and measurement accuracy.

SUMMARY OF THE INVENTION

According to the invention, there is provided an SPR sensor, comprising
a) an SPR device
b) a source of electromagnetic radiation from which radiation can be directed onto the device, and
c) a detector to measure the intensity of radiation reflected from the SPR device,
characterised in that the electromagnetic radiation contains TE-polarised and TM-polarised components and a polarisation analyser is interposed between the device and the detector such that, at angles away from resonance, little or no light reaches the detector.

According to a preferred aspect of the invention, there is provided a sensor for the qualitative and/or quantitative determination of a biological, biochemical or chemical analyte, which sensor comprises
a) an SPR device in the form of a block of material, which block has a layer of metallic material applied to at least part of a first surface thereof, the metallic layer in turn having a layer of material sensitive to the analyte applied to it,
b) a source of electromagnetic radiation, said radiation being directed onto said block in such a way as to be reflected off said part of said surface, and
c) a detector for measuring the intensity of the reflected radiation,
characterised in that the electromagnetic radiation contains TE-polarised and TM-polarised components and a polarisation analyser is interposed between the block and the detector such that, at angles away from resonance, little or no light reaches the detector.

The polarisation analyser may, for instance, comprise a polariser arranged such that its transmission axis is orthogonal to the resultant polarisation of the reflected beam.

For optimal results the incident radiation contains approximately equal amounts of the TE- and TM-polarised components. Away from resonance, the phases of both components behave in a similar way as the angle is changed. This allows a suitable analyser to be arranged so as to substantially prevent the polarised reflected light from reaching the detector at angles away from resonance.

Over the region in which SPR is excited, however, (i.e. as the angle of incidence of the radiation is altered) the phase of the TM-component changes, while the phase of the TE-component remains substantially unchanged. The TM-component also suffers some loss due to the SPR effect but despite this, the resultant polarisation of the reflected beam now has a component that can be transmitted through the analyser, and a signal is detected by the detector. The magnitude of this transmitted component, and hence the signal, increases until the phase change of the TM-component, due to the excitation of SPR is $\pi$ at the centre of the resonance. As the phase change increases to $2\pi$, the polarisation once more becomes perpendicular to the transmission axis and the signal falls again to zero.

Light may be coupled into the SPR device by conventional means, e.g. using a prism or a grating.

The sensor according to the invention is advantageous in that at resonance an increase in the light transmitted by the polariser occurs. This increase in light intensity is more easily detected than the reduction in light intensity usually detected in SPR measurements, enabling the use of a simpler and less costly detectors in some experimental configurations, as well as being more easily measurable, thereby improving the accuracy and sensitivity of the determination. In addition, the parameters of the device, notably the thickness of the metallic layer, are less critical.

In practice, even away from resonance, the phase changes of the TE- and TM-components following total internal reflection are somewhat different. This results in an elliptical polarisation of the reflected beam which can be compensated by an appropriate phase compensator. Suitable compensators will be apparent to those skilled in the art and include Babinet and Soleil compensators. The compensator may be located anywhere between the light source and the polariser.

The resonant condition is detected by varying the angle of incidence of the radiation from the source, either by varying the angle of incidence sequentially or by simultaneously irradiating at a range of wavelengths.

The nature of the coated block, the source of electromagnetic radiation and the detector will be apparent to those familiar with conventional SPR devices. By way of example, attention may be drawn to European Patent Application No 0305109 (Amersham) which describes such a device. In summary:

the block is conveniently of glass, e.g. in the form of a glass slide, the metallic coating is most conveniently of silver, the sensitive layer will generally be sensitised by having suitable biomolecules (e.g. specific binding partners for the analyte under test or analogues of the analyte) immobilised upon it, suitable such biomolecules and methods for their immobilisation being apparent to those skilled in the art, the light source is any source which has a small spectral width and good coherence, e.g. a laser, and the detector may be being any of those conventionally employed, e.g. photomultipliers and charge-coupled devices. Since it is the position of a maximum of light transmission which is measured by the device of the present invention, rather than a minimum, it is however possible to use far simpler (and hence cheaper) detectors than is necessary for conventional SPR when simultaneously irradiating at a range of angles. An example would be a position-sensitive detector which is much cheaper than, for example, a charge-coupled device. This is another significant advantage of the present invention.

DESCRIPTION OF THE DRAWINGS

An embodiment of the present invention will now be described by way of illustration only, with reference to the accompanying drawings in which.

DESCRIPTION OF A PREFERRED EMBODIMENT

Figure 1:
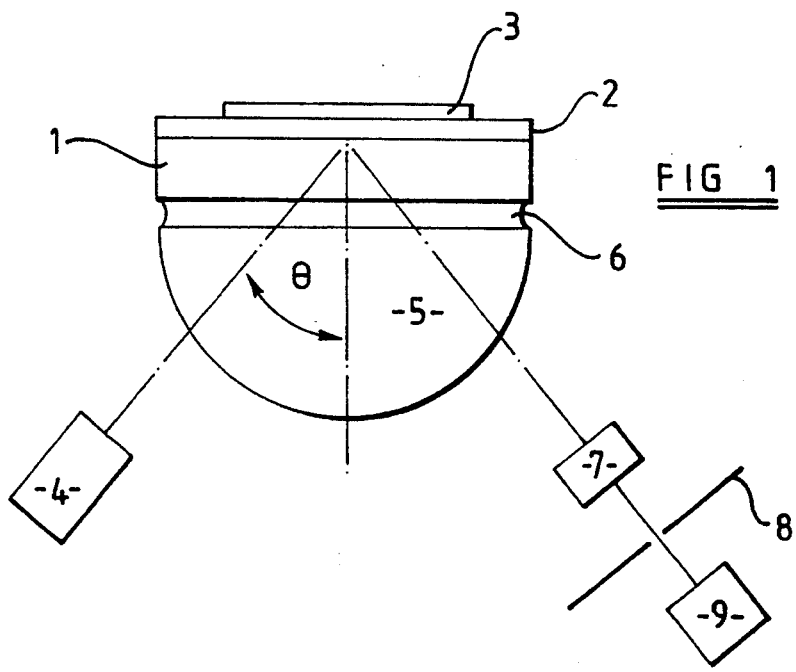
FIG. 1 is a schematic view of a sensor according to the invention.

Referring first to FIG. 1, a biosensor for the determination of an antigen in a sample of body fluid comprises a glass slide (1) coated with a thin layer of silver (2) which in turn is coated over a part of its surface with a layer (3) of immobilised antibodies to the antigen under test. Light from a laser light source (4) is coupled into the slide (1) by a hemicylindrical prism (5) and a layer of index matching fluid (6). The light contains both TE- and TM-polarised components of approximately equal magnitude.

Total internal reflection occurs at the glass-silver interface and the reflected beam is coupled out of the slide (1) by the matching fluid (6) and prism (5). Differences in the phase shifts of the TE- and TM-components are corrected by a compensator (7).

A polariser (8) is arranged between the compensator (7) and a position-sensitive detector (9). The transmission axis of the polariser (8) is arranged, when the device is out of resonance, to be perpendicular to the resultant polarisation of the reflected beam.

Figure 2:
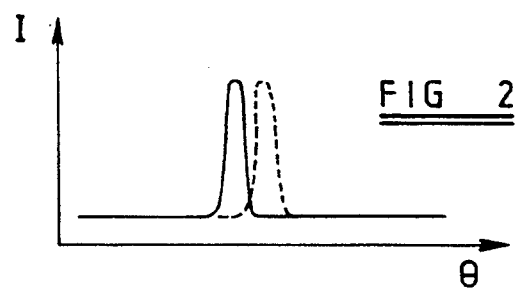
FIG. 2 shows the signal measured by a detector forming part of the sensor of FIG. 1, FIG. 3a and 3b are vector diagrams showing the phase change occurring in the TM-component at resonance.

The angle of incidence $\theta$ of the light from the laser (4) may be varied through a range of angles in which the resonance occurs. Far from resonance, there is little or no transmission of the reflected beam through the polariser (8) and no signal is detected. As resonance is approached, the component of the reflected beam along the transmission axis of the polariser (8) increases and subsequently decreases as the resonant condition is passed. A peak in the measured light intensity is observed (see FIG. 2). When a sample containing the antigen under test is brought into contact with the layer of immobilised antibodies (3), complexation occurs which changes the refractive index of the sensitive layer and hence the position of the resonance, as shown by the dotted line in FIG. 2.

Figure 3A:
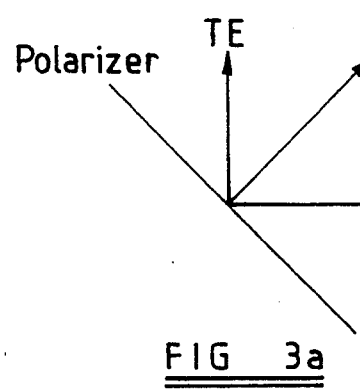
Figure 3B:
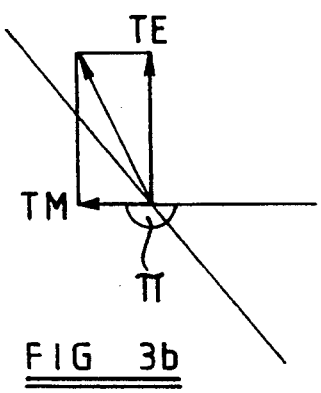

The effect of resonance on the phases of the TE- and TM-components is shown in FIG. 3. Far from resonance, the transmission axis of the polariser (8) is perpendicular to the resultant polarisation (the sum of the TE- and TM-components) as shown in FIG. 3a. At the centre of the resonance, the TM-component is shifted in phase (typically by $\pi$ radians) and also suffers some loss of magnitude (see FIG. 3b). At this point, the resultant has a component along the transmission axis and some light is transmitted. As the resonant condition is passed the phase shift of the TM-component increases to $2\pi$, returning the system to the situation shown in FIG. 3a.

Figure 4:
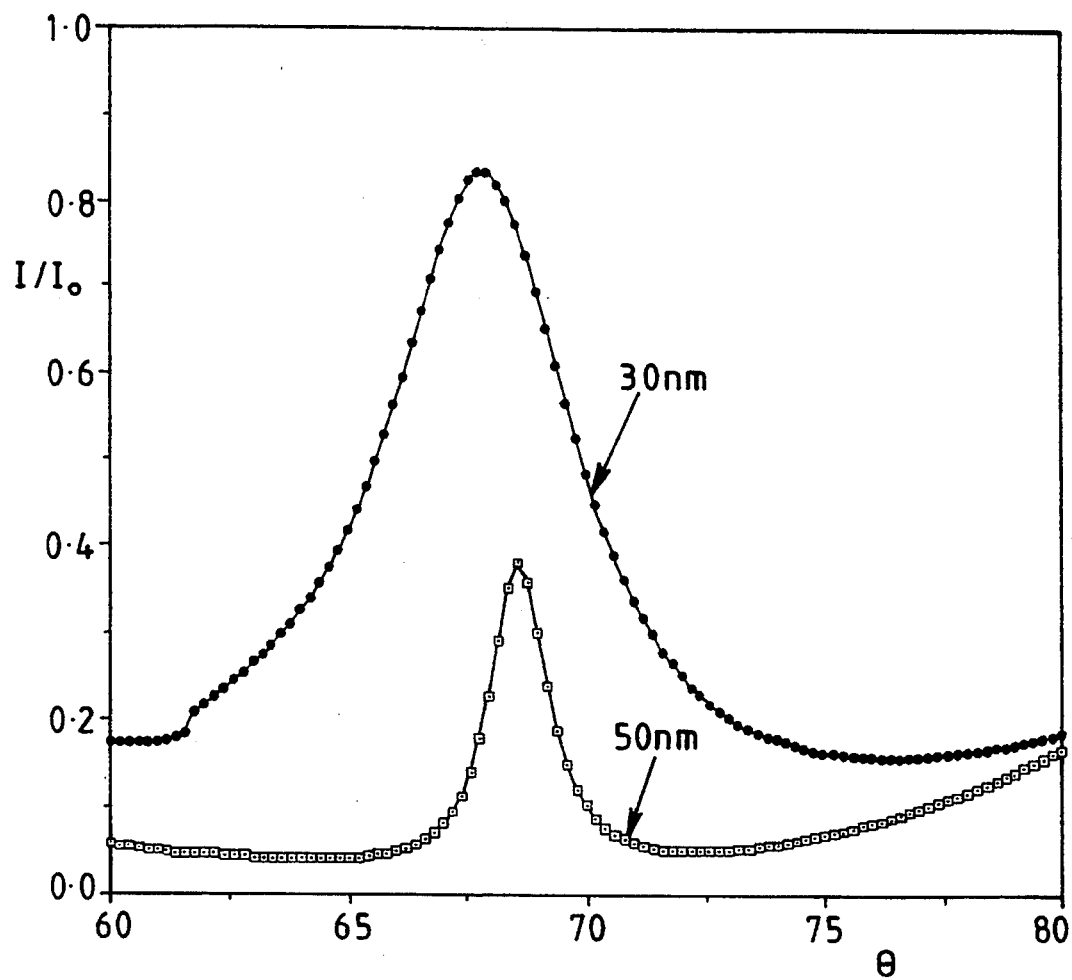
FIG. 4 is a theoretical plot of signal intensity against angle of incidence for a sensor according to the invention.
Figure 5A:
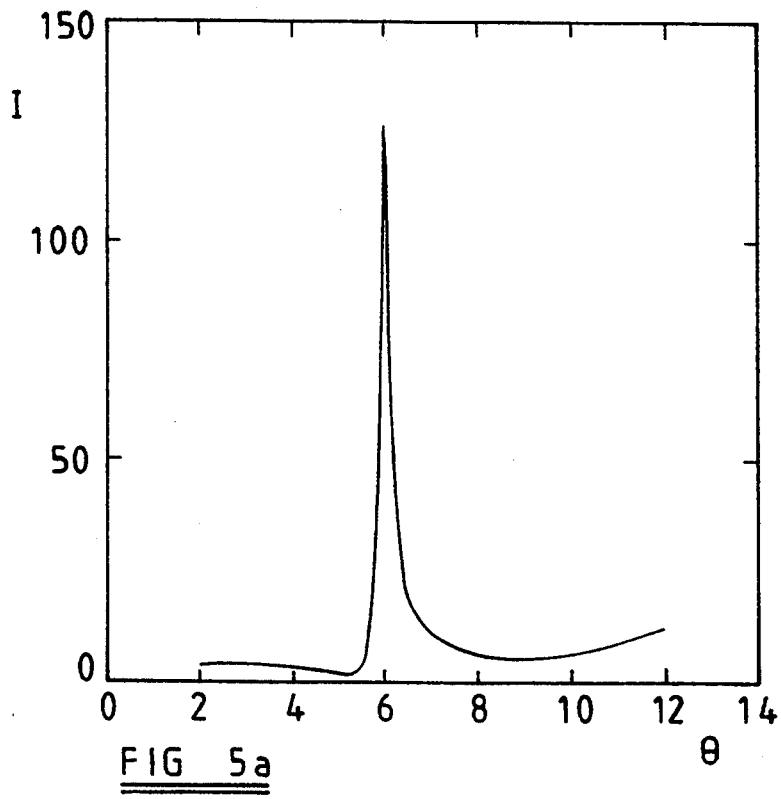
FIG. 5 shows actual experimental data obtained using a sensor according to the invention.
Figure 5B:
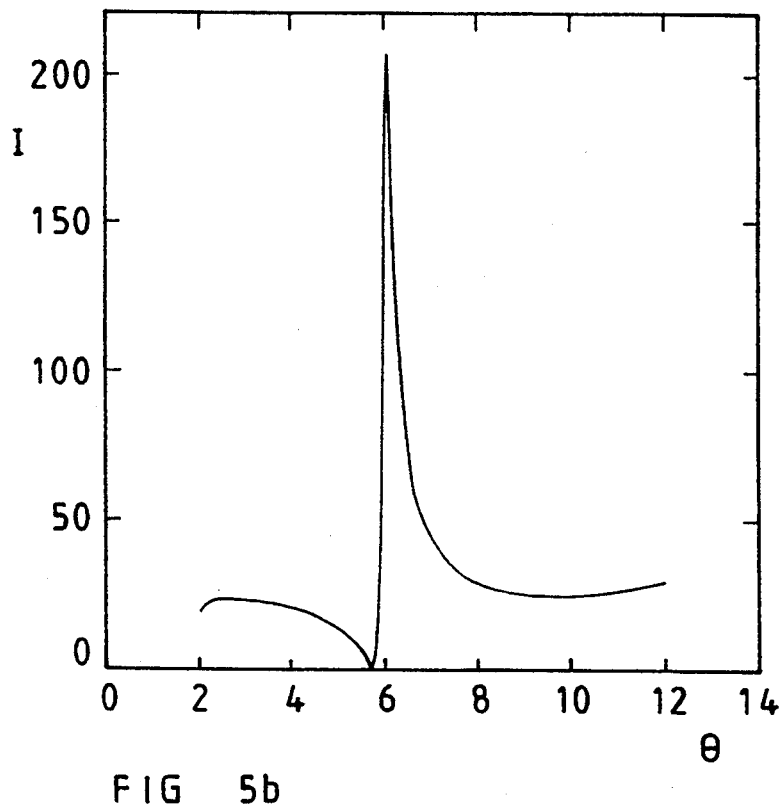

A theoretical plot of the ratio of the measured intensity $I$ and incident intensity $I_0$ as a function of the angle of incidence $\theta$ is shown in FIG. 4 for an SPR device, comprising a layer of silver on a BK7 substrate, in contact with water for two different thicknesses of silver. FIG. 5 shows experimental data obtained using a grating SPR device of detected signal intensity $I$ (in arbitrary units) against angle of incidence $\theta$, both with (FIG. 5a) and without (FIG. 5b) compensation of elliptical polarisation of the reflected beam due to differences in the phase changes of the TE- and TM-components.

I claim:

1. A surface plasmon resonance (SPR) sensor, comprising
   (a) an SPR device in the form of a block of dielectric material having a first surface, and a metallic material applied to said first surface of said block so as to create a metallic-dielectric boundary,
   (b) a source of electromagnetic radiation from which electromagnetic radiation can be directed onto said boundary such that total internal reflection occurs,
   (c) a detector to measure the intensity of electromagnetic radiation reflected from said SPR device, and
   (d) a polarization analyzer interposed between said SPR device and said detector such that, at angles resonance, little or no electromagnetic radiation reaches said detector,
   wherein said source of electromagnetic radiation is arranged such that the electromagnetic radiation directed onto said boundary contains TE(Transverse Electric)-polarized and TM(Transverse Magnetic)-polarized components.

2. A sensor for the qualitative or quantitative determination of a biological, biochemical or chemical analyte, which sensor comprises
   (a) a surface plasmon resonance device in the form of a block of material having a first surface, a layer of metallic material applied to at least part of said first surface forming a metallic-dielectric boundary, and a layer of material sensitive to the analyte applied to said layer of metallic material,
   (b) a source of electromagnetic radiation, said electromagnetic radiation being directed onto said block in such a way as to be reflected off said boundary, and said source of electromagnetic radiation being arranged such that the electromagnetic radiation contains TE(Transverse Electric)-polarized and TM(Transverse polarized components, (c) a detector for measuring the intensity of radiation reflected from said boundary, and (d) a polarization analyzer interposed between said block and said detector such that, at angles away resonance, little or no electromagnetic detector.

3. A sensor as claim in claim 1, wherein said polarization analyzer comprises a polarizer arranged such that its transmission axis is orthogonal to the resultant polarization of radiation reflected from said boundary.

4. A sensor as claimed in claim 1, wherein the radiation directed onto said boundary contains approximately equal amounts of the TE- and TM-polarized components.

5. A sensor as claimed in claim 1, further comprising a phase compensator located between said source of electromagnetic radiation and said polarization analyzer.

6. A sensor as claimed in claim 1, wherein said block is of glass.

7. A sensor as claimed in claim 1, wherein said layer of metallic material is of silver.

8. A sensor as claimed in claim 2, wherein said layer of material sensitive to the analyte is a layer of biomolecules immobilized upon said layer of metallic material.

9. A sensor as claimed in claim 1, wherein said source of electromagnetic radiation is a laser.

10. A sensor as claimed in claim 1, wherein said detector is a position-sensitive detector.

11. A method for the quantitative or qualitative determination of a biological, biochemical or chemical analyte in a sample, which method comprises the steps of (a) contacting the sample with the sensitive area of a surface plasmon resonance (SPR) device in the form of a block of material, which block has a layer of metallic material applied to at least part of a first surface thereof forming a metallic-dielectric boundary, the sensitive area being a layer of material sensitive to the analyte coated on the metallic layer, (b) directing electromagnetic radiation into the block in such a way that said radiation is reflected off said boundary, said radiation containing both TE(-Transverse Electric)- polarized and TM(Transverse Magnetic)-polarized components, and (c) measuring with a detector the intensity of radiation reflected from the SPR device and passing through a polarization analyzer interposed between the SPR device and the detector.

* * * * *